United States Patent
Wiktor et al.

(10) Patent No.: US 10,702,643 B2
(45) Date of Patent: Jul. 7, 2020

(54) DEVICE AND METHOD FOR REGULATING AND PRESETTING THE PUMP RATE OF BLOOD PUMPS

(71) Applicant: Fresenius Medical Care Deutschland GmbH, Bad Homburg (DE)

(72) Inventors: Christoph Wiktor, Gelnhausen (DE); Arne Peters, Bad Homburg (DE); Alexander Heide, Eppstein (DE); Manfred Weis, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 637 days.

(21) Appl. No.: 15/108,841

(22) PCT Filed: Jan. 21, 2015

(86) PCT No.: PCT/EP2015/051045
§ 371 (c)(1),
(2) Date: Jun. 29, 2016

(87) PCT Pub. No.: WO2015/110437
PCT Pub. Date: Jul. 30, 2015

(65) Prior Publication Data
US 2016/0325034 A1    Nov. 10, 2016

(30) Foreign Application Priority Data
Jan. 22, 2014   (DE) .................... 10 2014 000 678

(51) Int. Cl.
*A61M 1/10*  (2006.01)
*A61M 1/36*  (2006.01)

(52) U.S. Cl.
CPC ........ *A61M 1/1086* (2013.01); *A61M 1/3639* (2013.01); *A61M 1/3666* (2013.01);
(Continued)

(58) Field of Classification Search
CPC .............. A61M 1/1086; A61M 1/3667; A61M 1/3639; A61M 1/3666; A61M 1/1006;
(Continued)

(56) References Cited

U.S. PATENT DOCUMENTS

| | | | |
|---|---|---|---|
| 4,610,656 A | 9/1986 | Mortensen | |
| 5,965,089 A | 10/1999 | Jarvik et al. | |

(Continued)

FOREIGN PATENT DOCUMENTS

| | | |
|---|---|---|
| CN | 102458499 | 5/2012 |
| DE | 3326785 | 2/1985 |

(Continued)

*Primary Examiner* — Philip R Wiest
(74) *Attorney, Agent, or Firm* — Jacobson Holman, PLLC.

(57) ABSTRACT

For regulating and presetting the pump rate of a blood pump, a device and a method are configured for monitoring blood pressure values upstream and/or downstream from the blood pump. The monitored values, or another value formed from the monitored values, are compared with a limit value, which depends on an operating parameter or a pump parameter of the blood pump. In violation of the limit value, the pump rate of the blood pump is modified to such an extent, or a new pump rate is determined, such that the limit value is no longer violated or the degree of violation is reduced.

15 Claims, 4 Drawing Sheets

(52) U.S. Cl.
CPC ........... *A61M 1/3667* (2014.02); *A61M 1/101* (2013.01); *A61M 1/1006* (2014.02); *A61M 1/1012* (2014.02); *A61M 1/1039* (2014.02); *A61M 2205/3365* (2013.01)

(58) Field of Classification Search
CPC .. A61M 1/1012; A61M 1/1039; A61M 1/101; A61M 2205/3365
See application file for complete search history.

(56) References Cited

U.S. PATENT DOCUMENTS

| 2003/0045772 | A1 | 3/2003 | Reich et al. | |
|---|---|---|---|---|
| 2012/0150089 | A1* | 6/2012 | Penka | A61M 1/101 |
| | | | | 604/4.01 |
| 2012/0310135 | A1* | 12/2012 | Bauer | A61M 1/36 |
| | | | | 604/6.11 |

FOREIGN PATENT DOCUMENTS

| DE | 19849787 | 2/2000 |
|---|---|---|
| EP | 0513421 | 11/1992 |
| EP | 2517740 | 10/2012 |

* cited by examiner

DEVICE AND METHOD FOR REGULATING AND PRESETTING THE PUMP RATE OF BLOOD PUMPS

BACKGROUND OF THE INVENTION

1. Field of the Invention

The invention relates to the field of regulation of blood pumps in medical technical devices, in particular in blood treatment devices such as dialysis machines.

2. Description of Related Art

Blood treatment machines are medical technical machines for treating a patient's blood, usually extracorporeally. For example, medicines may be added to the blood or blood constituents may be removed from the blood or it may be heated or cooled. For this purpose, the blood is often pumped outside of the body by a blood pump, then treated and returned back to the patient's body. Such a blood circulation is known as an extracorporeal blood circulation.

The present invention will be explained in detail below on the example of a dialysis machine as an embodiment of a medical technical device for an extracorporeal blood treatment.

Additional blood treatment devices, for example, devices to support heart-lung activity, such as blood oxygenators or devices to support liver function by removing toxins from blood by adsorption. Devices to support liver function often combine dialysis methods and adsorption methods in one machine, such as the machine by the present applicant known by the brand name Prometheus, for example.

Dialysis machines or blood treatment machines in which blood from a patient is supplied to a blood treatment component through a blood line, treated by the blood treatment component and returned to the patient through the fluid line, which can be divided into an arterial branch and a venous branch. Examples of such blood treatment machines include in particular hemodialysis machines. One such blood treatment machine is the subject matter of DE 198 49 787 C1 by the present applicant, the contents of which are herewith fully incorporated into the disclosure content of the present patent application.

Dialysis is a method for purifying the blood of patients with acute or chronic renal insufficiency. A fundamental distinction is made here between methods having an extracorporeal blood circulation such as hemodialysis, hemofiltration or hemodiafiltration, and peritoneal dialysis, in which there is no extracorporeal blood circulation.

In hemodialysis, blood is carried in an extracorporeal circulation through the blood chamber of a dialyser, which forms the blood treatment component and is separated from a dialysis fluid chamber by a semipermeable membrane. The dialysis fluid chamber has a dialysis fluid which contains the blood electrolytes in certain concentrations flowing through it. The concentration of blood electrolytes in dialysis fluid corresponds to the concentration in the blood of a healthy person. During the treatment, the patient's blood and the dialysis fluid are generally passed in countercurrent along both sides of the semipermeable membrane at a predetermined flow rate. The substances that must be eliminated in urine, diffuse through the membrane from the blood chamber into the chamber for dialysis fluid, while at the same time, electrolytes present in the blood and in the dialysis fluid are diffusing from the chamber with the higher concentration to the chamber with the lower concentration. If a pressure gradient is established on the dialysis membrane from the blood side to the dialysate side, for example, by a pump drawing dialysate from the dialysate circulation downstream from the dialysis filter and the dialysate side, water is then transferred from the patient's blood through the dialysis membrane into the dialysate circulation. This ultrafiltration process leads to the desired withdrawal of water from the patient's blood.

In hemofiltration, ultrafiltrate is withdrawn from the patient's blood by applying a transmembrane pressure in the dialyser without passing the dialysis fluid by the side of the membrane of the dialyser opposite the patient's blood. In addition, a sterile and pyrogen-free substitute solution may be added to the patient's blood. We speak of predilution or postdilution, depending on whether this substitute solution is added upstream or downstream from the dialyser. The mass exchange takes place by convection in hemofiltration.

Hemodiafiltration combines the methods of hemodialysis and hemofiltration. There is a diffusive mass exchange between the patient's blood and the dialysis fluid through the semipermeable membrane of a dialyser, and the plasma water is also filtered through a pressure gradient on the membrane of the dialyser.

The methods of hemodialysis, hemofiltration and hemodiafiltration are usually performed with automatic hemodialysis machines such as those distributed by the applicant under the designation 5008, for example.

Plasmapheresis is a blood treatment method in which the patient's blood is separated into blood plasma and its corpuscular components (cells). The separated blood plasma is purified or replaced by a substitution solution and the purified blood plasma or the substitution solution is returned to the patient.

Machines for extracorporeal blood treatment such as dialysis machines have extensive functions. To control these functions, machines for extracorporeal blood treatment are equipped with at least one control unit, which may be embodied as a CPU (central processing unit) or as a microcontroller. These machines are programmed by software programs.

Pumps of various designs used for pumping fluids in machines for extracorporeal blood treatment. These hose reel pumps are frequently used in medical technology because they permit a noncontact means of transport of a fluid. In addition, they theoretically supply a flow rate that is proportional to the rotational speed over a wide range, regardless of the flow resistance upstream and downstream from the pump. In the case of a blood pump in an extracorporeal treatment process, the supplying (suction) side is referred to as the arterial side, where the vacuum established is typically approximately −100 to −300 mmHg (mercury column with respect to atmospheric pressure) and the discharging side is referred to as the venous side with an excess pressure that is established with respect to external pressure.

DE 3 326 785 A1 shows a typical design for such an occlusive hose reel pump, according to which the pump medium is moved by means of a periodically occluded hose.

In terms of the basic concept, a reel pump has a stator and a rotor. The stator is formed on the pump housing and has a recess with whose continuous vertical wall a pump hose is in contact. The range in which the pump hose is in contact with the wall forms the pump bed, which has the contour of a circular cutout.

The axis of rotation of a rotor having rotatably mounted reels on its free ends passes through the midpoint of this circular cutout. The reels come in contact with the pump hose, which is itself in contact with the circular contour of the pump bed, with the rotation of the rotor in the working direction compressing the hose or the bed so much with further rotation that it closes off the hose (occlusively) in a fluid-tight manner.

By rolling the reels further on the pump hose, the pump medium in the pump hose is transported further. In most cases, such a reel pump has two reels, which are mounted on the rotor in such a way that the connecting line runs through their axes of rotation on the rotor through the axis of rotation of the rotor.

Other types of pumps, which may be used in machines for extracorporeal blood treatment, include centrifugal pumps, diaphragm pumps or gearwheel pumps, for example.

The type of pump is definitive for the stress on the medium to be pumped. This is important in particular in an extracorporeal blood circulation because the blood may be damaged by pumping and in particular the erythrocytes, i.e., the red blood cells, may be destroyed (hemolysis). This may happen mechanically, for example, due to squeezing in a hose carrying blood, as well as due to excessively high pressures or pressure gradients.

The pulsatile, nonsteady flow which is caused by the continuous action of the reels in the pump hose segment is characteristic of a hose reel pump. On engagement of the reels in the hose segment, the hose is squeezed and liquid is thereby displaced. This liquid is displaced both in and against the direction of flow. Upstream from the reel, the displaced liquid is superimposed on the flow in the direction of the pump in ongoing operation and thus leads to a short-term net reduction in the flow, so that the arterial pressure becomes less negative until the hose is completely occluded. Then the liquid in the hose is accelerated again and the arterial pressure drops further. Downstream from the hose reel pump there is a sudden drop in pressure as soon as the reel emerges from the pump segment and there is an equalization of pressure between the vacuum in the previously enclosed segment between the reels and the excess pressure downstream from the pump.

Pressure peaks (and/or flow peaks) in the area of the puncture site of the needle, which returns the extracorporeal blood to a patient, may occur and cause shearing forces, which, in the extreme case, may lead to thrombosis (formation of clots) on the vascular walls and to hemolysis, i.e., to destruction of erythrocytes (red blood cells). Upstream from the pump, there may also be high shearing forces in equalization between the high-pressure system and the low-pressure system.

Another type of pump used in machines for extracorporeal blood treatment is the impeller pump or centrifugal pump. Centrifugal pumps contain essentially a housing to accommodate an impeller wheel. This impeller wheel may be rotated by an axis running through the housing in one embodiment. According to an alternative embodiment, the impeller wheel is rotated without contact. The impeller wheel here is fixedly connected to a magnet, for example, and can be excited to rotation by a rotating magnetic field which is generated by field coils, for example, is applied externally and can be excited to rotate by magnetic coupling. The rotating impeller wheel moves the liquid in the housing from a liquid inlet to a liquid outlet. Due to the active principle, centrifugal pumps supply a constant differential pressure, wherein the output pressure of the pumped liquid depends on the input pressure, the viscosity of the liquid, the pump rate and the rotational speed. Pressure pulses in the fluid being pumped, as is the case with peristaltic pumps, do not occur with centrifugal pumps in normal operation at a constant rotational speed of the impeller wheel. This reduces the hemolysis induced by pulsatile pumping of blood.

Increased hemolysis can be a serious risk to the patient. Thus, in addition to anemia, inflammations, hepatic stress and an increased risk of thrombosis are some of the direct consequences of a release of the hemoglobin, which is responsible for the transport of oxygen, from the erythrocytes. In addition to hemoglobin, the electrolyte potassium also leaks out of damaged cells. Increased release of potassium interferes with stimulus conduction in nerves and muscles and may even trigger acute cardiac problems.

Regardless of the type of blood pump used, there is in general the risk of damaging the cellular constituents of blood in the pumping of blood.

SUMMARY OF THE INVENTION

The object of the present invention is therefore to create a device and a method which will reduce the incidence of damage incurred by blood when pumped.

These objects are achieved according to the invention by the method and the device described herein.

Advantageous embodiments are the subject matter of the dependent claims.

In one embodiment, it is provided that a new pump rate of a blood pump is to be established for pumping blood if the blood pressure upstream and/or downstream from the blood pump with a currently prevailing pump rate violates a limit value that depends on an operating parameter or a pump parameter of the blood pump. This new predetermined blood pump rate would result in the limit value no longer being violated and/or the difference in the blood pressure upstream from this limit value and/or downstream from the blood pump being reduced by this limit value.

In particular the pump rate, i.e., the volume pumped per unit of time, as well as the resulting blood pressures upstream and downstream from the blood pump are of special importance as operating parameters for blood pumps.

In addition, it is provided that the device adjusts the pump rate thereby predefined.

It has been found that it is unavoidable in pumping blood through an extracorporeal blood circulation that certain shearing forces act on the blood cells. If these forces exceed a certain measure, the cells are damaged. This is associated with a blood damage incidence.

In addition, extremely small air bubbles are introduced into the bloodstream upstream and in the pump when there is a great vacuum, for example, lower than −300 mmHg or −400 mmHg in comparison with ambient pressure.

This occurs, firstly, due to leakage at the connection points and addition points, such as a connector, for example, through which anticoagulants such as heparin are added to the extracorporeal blood circulation and, secondly, due to degassing in the blood.

It is difficult to separate these microbubbles from the extracorporeal blood circulation because of their small size. If they enter the patient, they can result in occlusion of capillary vessels, which has a negative effect on the patient's well-being.

The invention is based on the finding that the height of the blood pressure upstream and downstream from the blood pump and/or the difference between these pressures and the blood flow rate are definitely responsible for the occurrence of blood damage such as hemolysis in pumping blood with centrifugal pumps. In addition, depending on the type of pump, the pump rate, i.e., the volume of blood pumped per unit of time also affects the incidence of blood damage.

With centrifugal pumps the release of hemoglobin detected, which is a measure of the incidence of hemolysis as blood damage, is largely independent of the blood flow rate but tends to be greater with an increase in blood pressure. The blood pressure can fundamentally be evaluated upstream or downstream from the centrifugal pump because the liquid pressures upstream and downstream from the pump in the case of a centrifugal pump are linked to one another via the pump rate of the centrifugal pump and a characteristic line for the centrifugal pump.

This is a direct result of the non-occluding pump principle of centrifugal pumps. Thus, both the height of the blood pressure upstream and downstream from the centrifugal pump and the difference between these pressures can be equated, with respect to the pump rate, to obtain a statement about the blood damage to be expected.

Hose reel pumps are occluding pumps in normal operation, where at least one reel of the pump completely occludes the hose between the pump inlet and the pump outlet, Therefore, there is no direct relationship between the liquid pressures upstream and downstream from the hose rotary pump because, with hose reel pumps, the pump inlet and the pump outlet are isolated from one another in a pressure-proof manner in the normal case.

The rotational speed, which largely determines the pump rate, the viscosity of the medium pumped and the flow resistances of the flow paths upstream and downstream from the hose reel pump are the important parameters for the pressure conditions in hose reel pumps. In blood pumps, for example, these flow resistances are determined by the blood hoses, the cannulas and the dialysis filters.

Dialysis filters may become blocked during a dialysis treatment (so-called clotting) and the patient's blood may become thicker during the treatment due to the withdrawal of excess plasma water, so that the flow resistances and the viscosity of the blood may change, which may result in altered blood pressures in the extracorporeal blood circulation in the course of a treatment.

Thus, with an extremely elevated flow resistance downstream from the hose reel pump, there may be peaks in the blood pressure, which entail the risk that leaks may occur in the connected hose segments or in the dialysis filter, causing the patient's blood to enter the dialysis circulation or even to escape into the environment.

To prevent such a situation, hose reel pumps for pumping blood are normally equipped with spring-mounted hose reels. If the force created due to the blood pressure on the hose reels exceeds the spring force with which the reel is pressed against the hose, the reel is moved radially to the direction of revolution to the axis of rotation, so that the reel no longer completely occludes the hose.

Excessively high blood pressure is reliably prevented in this way. If an operating condition in which the blood pressure downstream from the hose reel pump exceeds the spring force of the hose reels with which the hose being inserted is pressed against the pump bed, this is associated with a marked increase in hemolysis.

In the normal case, i.e., with occlusive pumping, the release of hemoglobin by hose reef pumps is largely independent of the blood pressure and is proportional to the pump rate.

In blood treatments and in particular in hemodialysis treatments, the blood flow rate is a definitive treatment parameter which is usually preselected by the medical personnel and is entered into the dialysis machine as a target value by way of a user interface. This establishes the pump rate of the blood pump accordingly and maintains the preselected blood flow rate largely without taking into account the blood pressure at various locations in the extracorporeal blood circulation. Only exceeding a limit value for the pressure can result in an interruption in or termination of the treatment, where the blood pump can be stopped and an alarm can be sent to the operator.

The blood pump may be a hose reel pump or a centrifugal pump, for example.

Due to the different characteristics of the two pump principles, there are operating parameters for which the expected blood damage is lower than with otherwise comparable blood treatment machines equipped with hose reel pumps for pumping blood if the centrifugal pump and hose reel pump deliver blood at identical pump rates due to the different characteristics of the two pump principles.

On the other hand, however, it may occur in therapeutic practice that the pump rate of the centrifugal pump initially set leads to operating parameters at which, from the standpoint of damage to the blood, there is a disadvantage to the use of centrifugal pumps for pumping blood in comparison with the otherwise comparable blood treatment machines equipped with a hose reel for pumping blood.

One embodiment of the invention therefore provides that in such a case, the pump rate of the centrifugal pump is to be varied, so that the incidence of damage to blood to be expected is at least lower and/or operation is no longer a disadvantage in comparison with a blood treatment machine that is equipped with a hose reel pump for pumping blood and pumps the blood at an identical pump rate.

Another embodiment of the invention provides that with blood treatment machines equipped with hose reel pumps for pumping blood, the pump rate initially set in the event such operating parameters result from this due to which the blood pressure would become so great downstream from the hose reel pump that the occlusive force of the pump, i.e., the spring force with which the reels of the hose reel pump press the enclosed hose again, the occlusive force of the pump is no longer sufficient to completely occlude the blood hose, to reduce it to the extent that the blood pressure downstream from the hose reel pump is lower than the limit value corresponding to the occlusive force for the blood pressure. The occlusive force here is a pump parameter characteristic of the hose reel pump.

The goal of all these embodiments is for the blood to be damaged as little as possible.

BRIEF DESCRIPTION OF THE DRAWINGS

Additional details and advantages of the invention will now be described in greater detail on the basis of exemplary embodiments illustrated in the drawings in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
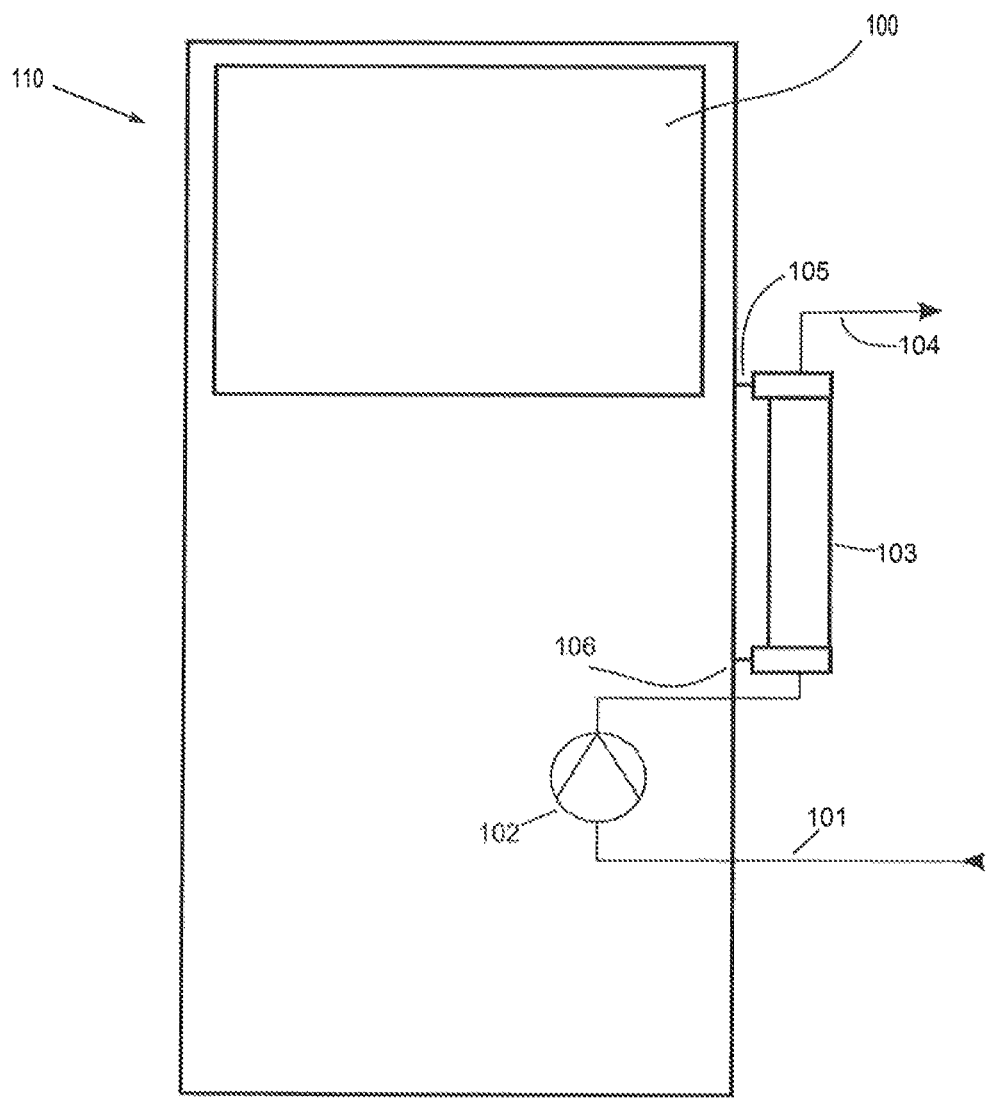
FIG. 1 shows a schematic diagram of a blood treatment machine designed as a hemolysis machine in accordance with the teaching of the present invention.

FIG. 1 shows schematically a blood treatment machine embodied as a hemodialysis machine. The hemodialysis machine 110 comprises parts of an extracorporeal blood circulation with an arterial blood line 101, which draws blood from a patient (not shown), Then blood pump 102 pumps the blood through the hose segment enclosed in it through a dialyser 103 equipped with a semipermeable membrane that separates the extracorporeal blood circulation from a dialysis circulation in a semipermeable manner. The treated blood is returned to the patient through the venous line 104, The lines and hose segments that are used, in particular the parts forming the extracorporeal blood circulation, are usually disposable parts that are discarded after use. Dialysate is pumped through the dialysis lines 105 and 106 and through the dialyser 103, where it enters into a diffusive mass exchange with the patient's blood through the semipermeable membrane of the dialyser 103. If a pressure gradient is also built up from the blood side of the dialysis filter to the dialysate side of the patient, plasma water is expressed from the patient's blood into the dialysate. Water can thus be removed from the patient's blood. The dialysate is prepared in the hemodialysis machine 110 and discarded after use. The blood pump 102 may be designed as a centrifugal pump or as a hose reel pump, in accordance with the teaching of the present invention.

Centrifugal pumps may be used in particular as blood pumps in hemodialysis machines when the impeller wheel of the centrifugal pump is disposed in a cassette that is designed as a disposable part. The cassette may contain additional parts of the extracorporeal blood circulation in a fluid-tight connection, such as blood lines, clot catchers and drip chambers, for example. The driven impeller wheel is discarded together with the cassette after use. The means driving the impeller are accommodated in the hemodialysis machine and drive the impeller by way of a magnetic coupling.

The hemodialysis machine 110 is equipped with a control unit (not shown in FIG. 1), which can control and/or regulate the blood pump and is equipped with sensors to pick up blood pressures in the extracorporeal blood circulation. The control unit is configured so that it can execute the methods described here.

Figure 2:
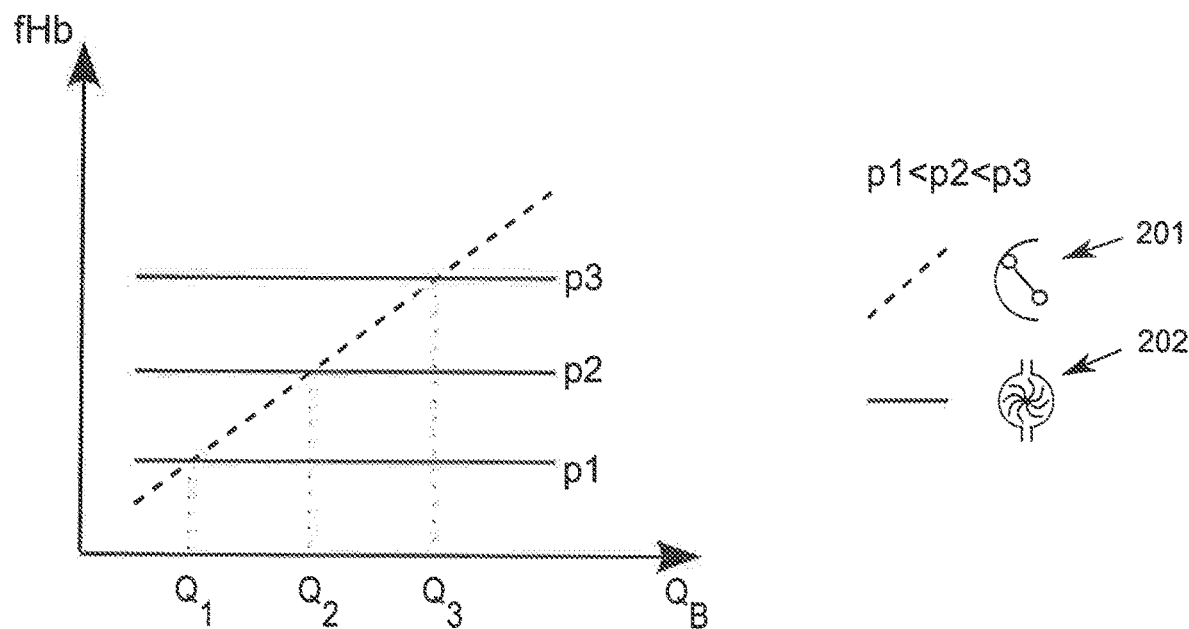
FIG. 2 shows a diagram illustrating the release of hemoglobin in pumping blood as a function of operating parameters in the use of centrifugal pumps and hose reel pumps in accordance with the teaching of the present invention.

FIG. 2 shows a diagram which represents schematically the blood damage for two blood treatment machines, one of which uses a centrifugal pump for pumping blood and the other of which uses a hose reel pump for the same purpose, but they are otherwise identical.

The dashed line here characterizes the blood treatment machine with the hose reel pump, represented by diagram 201. The solid lines apply to the blood treatment machine with the centrifugal pump, represented by diagram 202.

The blood flow rate $Q_B$ is plotted on the abscissa, and the value on the ordinate characterizes the formation of free hemoglobin (fHb).

The formation of free hemoglobin is largely independent of the blood pressure for the hose reel pump, whereas it correlates with the pressure in the case of the centrifugal pump (shown for three different pressures p1, p2, p3 in FIG. 2 as an example).

FIG. 2 shows that the blood damage with the centrifugal pump increases with an increase in the blood pressure downstream but is not influenced substantially by the blood flow through the centrifugal pump.

However, when using a hose reel pump, the blood damage in normal operation, i.e., with occluding pump reels, is essentially independent of the blood pressure downstream but it increases with an increase in the blood flow rate.

Thus, depending on the blood pressure p prevailing downstream from the pump for operation of the blood treatment machine with the centrifugal pump, this yields a preferred range for the blood flow rate $Q_B$ at which the blood damage turns out to be less than with a comparable machine having a hose reel pump and identical blood pressure p downstream from the hose reel pump. In the example in FIG. 2, this blood flow rate occurs at a pressure p1 between Q1 and the maximum allowed blood flow rate; at a pressure p2, it occurs between Q2 and the maximum allowed blood flow rate, and at a pressure p3, it occurs between Q3 and the maximum allowed blood flow rate.

In accordance with the teaching of the present invention, it is now possible to check on whether the blood flow rate is in this range, taking into account the prevailing blood pressures and the extracorporeal circulation during operation of a blood treatment machine, which uses a centrifugal pump to pump the blood.

If this is not the case, then the working point of the centrifugal pump, defined by the operating parameters of the pump rate and the blood pressure upstream or downstream from the pump or the difference between these blood pressures is located on the left side of the dotted line in FIG. 2. The control unit can then adjust the blood flow rate until it is at least on the dotted line.

With the change in the pump rate, the blood pressure also changes upstream and downstream from the centrifugal pump due to the relationship between flow rate, flow resistance and liquid pressure. With reference to FIG. 2, such an adjustment means that the working point of the centrifugal pump does not change on a horizontal line. An increase in the pump rate as well as a reduction in the pump rate can thus result in the working point of the centrifugal pump being adjusted again within the preferred range, namely on the dotted line in FIG. 2 or at the right of it.

In practice, it is found that the pressure downstream from the centrifugal pump increases with the square of the increase in the pump rate due to constrictions in the flow path downstream from the centrifugal pump, for example, at cannulas or catheters. The preferred change in the pump rate is therefore a reduction. In special cases, for example, when the working point lies only slightly to the left of the dotted line in FIG. 2 or when special hose sets are used for pumping blood, an increase may also result in the working point of the centrifugal pump being established again in the preferred range, namely on the dotted line or to the right of it in FIG. 2.

In one embodiment, the control unit may also adjust a new pump rate in an iterative process by varying the pump rate in a positive or negative direction only in small increments, namely in 1% increments, and there is a check after each step to ascertain whether the change has led to a reduction in the distance of the working point of the centrifugal pump from the dotted line in FIG. 2.

It is also conceivable that the control unit performs the change in the pump rate within therapeutically allowed limits both as an increase and as a reduction in this iterative process and thus determines the best possible new pump rate by documenting the blood damage incidence for each blood pump rate within the allowed range, for example, by saving it in a data memory and then setting that pump rate with the lowest documented blood damage. It is possible that no working point to the right of the dotted line is established for the blood pump rate within the limits allowed therapeutically. In this case, in accordance with the present invention, the pump rate with the lowest associated blood damage incidence is determined and/or set.

There is thus also a check on whether an operating parameter of the blood pump violates a limit value. This limit value depends on the blood pressure established previously. It is irrelevant here whether the blood pressure is measured upstream from the blood pressure or downstream from the blood pressure or whether the control unit is notified of this, because if the rotational speed of the centrifugal pump is known, the respective missing liquid pressure can be determined from a stored pump characteristic line.

This limit value, which corresponds to the interface between the solid line and the dotted line in FIG. 2, is in this case a blood flow rate, which depends on the prevailing blood pressure p downstream from the centrifugal pump, i.e., the pump rate of the centrifugal pump.

A violation of this limit value means that the centrifugal pump pumps at a pump rate which is a disadvantage and accordingly causes more blood damage than a hose reel pump installed in a comparable machine and having an identical pump rate. Consequently, the control unit of the blood treatment machine will modify and adjust the pump rate of the centrifugal pump until the pump rate is no longer a disadvantage as described above.

Since this adjusted pump rate is different from the pump rate initially set on the blood treatment machine, it is possible to check in advance on whether the adjusted pump rate is allowed in accordance with the patient's treatment.

It is conceivable that before the blood treatment machine adjusts the pump rate, a message will be issued to the treating medical personnel. For example, a corresponding message may be displayed on a screen, which must be acknowledged by the medical personnel through user input. In addition, it is conceivable for the machine to display a range of blood flow rates, for which the expected blood damage will turn out to be less than with a comparable machine using a hose reel pump and that the medical personnel will select a specific blood flow rate after considering the therapeutic consequences.

The curves shown in FIG. 2 can be determined in laboratory trials, for example, in which comparable machines equipped with centrifugal pumps and hose reel pumps are compared with one another under varying conditions with regard to blood pressure, blood flow rate and the resulting blood damage.

Comparative data obtained in this way can then be stored in the blood treatment machine either in the form of a table or in the form of mathematical descriptions derived from the experimental data. Regardless of how the data is stored, it is important only that the relationship between the blood pressure downstream from the centrifugal pump and the blood flow rates or the differential pressure between the pump inlet and the pump outlet and/or the rotational speed of the pump and the blood flow rates has been stored in the medical treatment machine.

Figure 3:
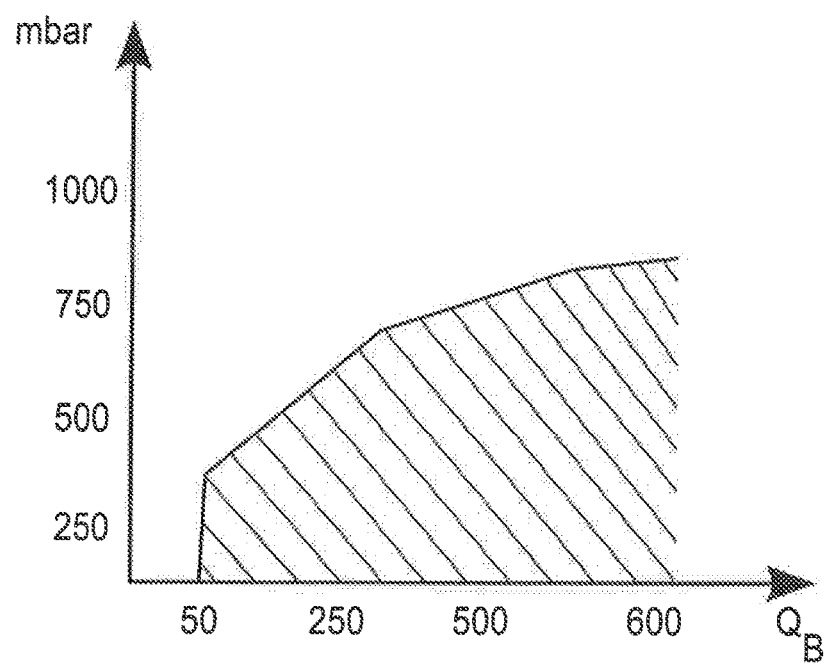
FIG. 3 shows another diagram which illustrates the regulating range for the pump rate for centrifugal pumps for pumping blood in accordance with the teaching of the present invention.

FIG. 3 shows an example of a diagram illustrating a preferred range for the operating point of the centrifugal pump, shown with hatching in FIG. 3, for a blood pump in the form of a centrifugal pump. The discontinuities in the upper limit of the hatched working range correspond to the points of intersection of the dotted line with the solid lines in FIG. 2. In this range, the differential pressure from the blood pressure downstream and the blood pressure upstream, plotted on the ordinate, and the blood flow rate form a ratio, such that no change in the pump rate is necessary.

If an operating point outside of the hatched range is established, the regulation intervenes in accordance with the teaching of the present invention, such that the pump rate of the centrifugal pump is varied until the working point is again within the hatched range.

The hatched range shown as an example in FIG. 3 may cover another range, depending on the embodiment of the blood pump on which it is based.

Figure 4:
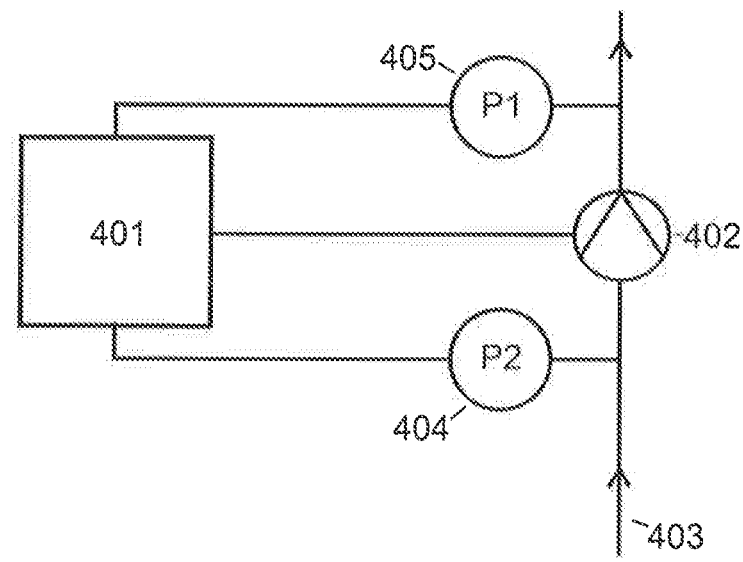
FIG. 4 shows a simplified schematic diagram of a blood treatment machine in accordance with the teaching of the present invention.

FIG. 4 shows a simplified schematic diagram of a blood treatment machine, which is configured for setting a pump rate of a blood pump in accordance with the teaching of the present invention. This comprises a control unit 401, embodied as a microcontroller, for example, which can control the pump rate of the blood pump 402. The measured values of the pressure sensors 404 and/or 405 upstream from the blood pump 402 (P1) and/or downstream from the blood pump 402 (P2) can be sent to the control unit. The blood pump conveys blood within a blood line 403, which may be part of an extracorporeal blood circulation, for example, during a hemodialysis treatment.

The control unit 401 is configured in accordance with the teaching of the present invention, so that a pump rate of the blood pump, which was previously made known to the control unit, for example, by input by an operator into an operator's interface, which may be embodied in the form of a touchscreen, for example, is to be adjusted by corresponding control signals to the blood pump 402 and if the blood pressure P2 upstream from the blood pump and/or the blood pressure P1 downstream from the blood pump and/or the difference between the blood pressure upstream and downstream from the blood pump violates a limit value, which depends on an operating parameter of the blood pump, then the pump rate of the blood pump is to be adjusted until the limit value is no longer violated.

It may be a violation of the limit value if the differential pressure P1-P2 is not within the hatched range as shown in FIG. 3, where the limit value depends on the pump rate as an operating parameter and wherein the blood pump is designed as a centrifugal pump. In response to that, the control unit can modify the pump rate of the centrifugal pump iteratively until the pressure difference P1-P2 determined from the pressure values P1 and P2 is again within the hatched range.

It may also be a violation of the limit value if the pressure P2 upstream from the pump, which may be embodied either as a hose reel pump or as a centrifugal pump, is lower than a limit value. In other words, below a certain critical vacuum in the blood, for example, 400 mbar below ambient pressure, there may be an increased incidence of microbubbles in the blood. To prevent this, the control unit may reduce the pump rate of the pump successively after detecting that the pressure P2 has dropped below the limit value, until the pressure P2 is again above this limit value. A reduction in the blood flow rate in favor of higher patient safety may thus be accepted. Likewise, the number of alarms triggered because of the appearance of microbubbles may also be reduced, if necessary.

A further violation of the limit value may occur when the blood pressure is below a limit value, which depends on the pump rate as an operating parameter of the blood pump, by analogy with FIG. 2, in the case when the blood pump is embodied as a centrifugal pump. In this case, the expected blood damage due to the centrifugal pump is better than that of a hose reel pump with an identical pump rate that is used for comparison. In this case, the control unit increases the pump rate of the centrifugal pump until the measured pressure downstream from the pump corresponds at least to the limit value. This limit value corresponds to the dotted line in the diagram in FIG. 2.

A further violation of the limit value may occur when the blood pressure downstream from the blood pump is above a limit value, which corresponds to the spring force of the spring-mounted pump reel (occlusive force) as an operating parameter in the event the blood pump is a hose reel pump. This limit value depends on the properties of the hose, such as the elasticity and diameter, enclosed in the pump bed and may be disclosed to the control unit in any desired manner, for example, by having the operator input the type of hose for the corresponding limit values being stored in a data memory which the control unit can access. If the limit value is violated, the control unit will reduce the pump rate of the hose reel pump until the measured pressure downstream from the blood pump no longer violates the limit value.

Figure 5:
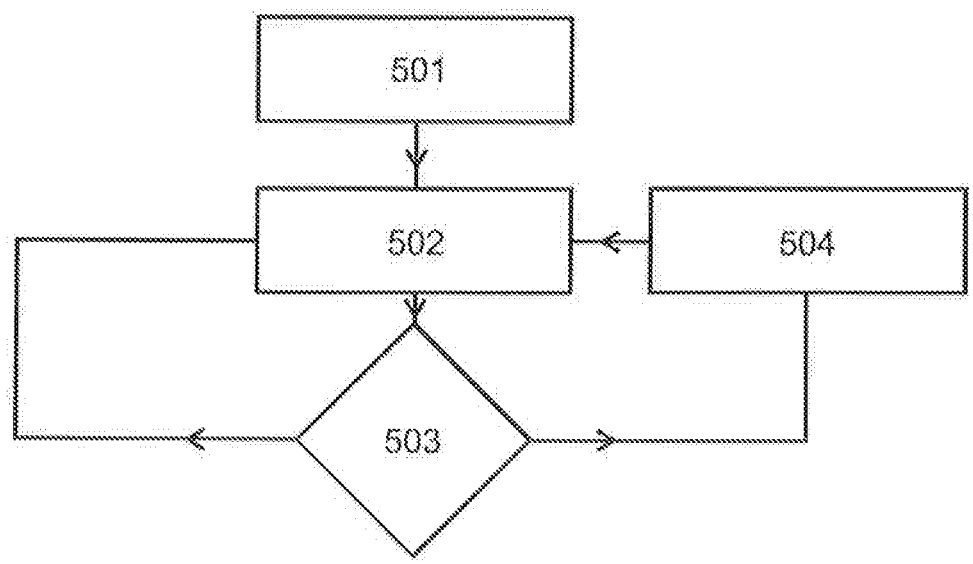
FIG. 5 shows a flowchart for an exemplary method for regulating the pump rate of pumps for pumping blood in accordance with the teaching of the present invention.

FIG. 5 shows a flowchart for an exemplary method for presetting the pump rate of pumps for pumping blood in accordance with the teaching of the present invention, if this method takes place on an apparatus according to FIG. 4.

An initial pump rate for a blood pump can be adjusted in step 501 or a previously adjusted pump rate is determined for this blood pump. In step 502, the blood pressure upstream and/or downstream from the blood pump is measured. The value thus determined or a value formed from this measured data, for example, the differential pressure being determined from the blood pressure readings upstream and downstream from the blood pump, is compared with a limit value in step 503. The limit value depends on at least one operating parameter or pump parameter of the blood pump, for example, with the prevailing pump rate or the occlusive force for the blood pump.

If the limit value is violated by the value thus ascertained, then in step 504 there is a change in the pump rate. This may mean an increase or a decrease in the pump rate. This change in the pump rate may take place in an (iterative) control loop consisting of steps 502, 503 and 504 until the limit value is no longer violated, such that with each change in the pump rate, a check is performed in step 503 to determine whether the limit value has been violated.

The pump rate is not changed if the limit value has not been violated. Nevertheless in steps 502 and 503, there is still constant monitoring of whether the limit value is violated.

It is also conceivable that the method according to FIG. 5 is performed in such a way that when a pump rate set initially for the blood pump or determined in step 501 leads to a violation of the limit value found in step 503, then in step 504, for each allowed pump rate, the entire therapeutically allowed range for the pump rate of the blood pump is run through in small increments of the pump rate and the blood damage characterized by the working point as in FIG. 2 for each allowed pump rate and the blood damage characterized by the working point according to FIG. 2, which is determined by the known pump rate and the blood pressures downstream and/or upstream from the blood pump in step 502 is recorded. To do so, the operating points so determined are stored for each allowed pump rate in a data memory and then the pump rate for which the resulting incidence of damage to blood is lowest (i.e., fHb in FIG. 2) is set and/or preselected.

A new pump rate, which is thereby determined and for which the resulting blood damage incidence is lowest, need not necessarily be associated with a working point of the blood pump, which is in the preferred range according to FIG. 3. In this case, the distance from the allowed range is minimal or as small as possible.

Figure 6:
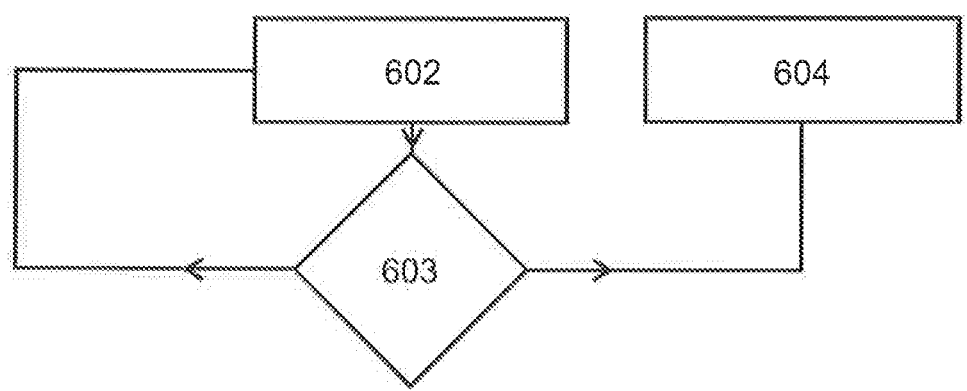
FIG. 6 shows a flowchart for an exemplary method for presetting the pump rate of pumps for pumping blood in accordance with the teaching of the present invention.

FIG. 6 shows a flowchart for an exemplary method for preselecting the pump rate of pumps for pumping blood in accordance with the teaching of the present invention.

In step 602 the blood pressure upstream and/or downstream from the blood pump is determined.

The value thus determined or a value formed from this measured data, for example, the differential pressure from the blood pressures upstream and downstream from the blood pump is compared with a limit value in step 603. The limit value depends on at least one operating parameter or pump parameter of the blood pump in a manner already described.

If the limit value is violated by the value thus determined, then step 604 a new pump rate is preselected so that the limit value would no longer be violated or the difference in the blood pressure upstream and/or downstream from the blood pump from this limit value would become smaller.

If the limit value is not violated, there is no preselection of a new pump rate. Nevertheless in steps 602 and 603 there is constant monitoring to ascertain whether the limit value is violated.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of controlling a centrifugal blood pump, said method comprising the steps of:
   determining a current pump rate of the centrifugal blood pump;
   determining a blood pressure upstream and/or downstream from the centrifugal blood pump; and
   controlling the centrifugal blood pump at a new Pump rate when the blood pressure upstream and/or downstream from the centrifugal blood pump, and/or a difference in the blood pressure values upstream and downstream from the centrifugal blood pump, violate a limit value, which depends on the pump rate of the centrifugal blood pump, which would result in the limit value no longer being violated or the difference in the blood pressure downstream from the centrifugal blood pump and the limit value, or upstream from the centrifugal blood pump and the limit value, decreasing,
   such that any damage to the blood being pumped by the centrifugal blood pump is less than or equal to the damage which would be associated with the blood being pumped by a hose reel pump in comparable service, and with an identical blood pressure downstream therefrom, with the step of controlling including a determination of any damage to the blood being pumped by the centrifugal blood pump relative to damage to the blood which would be associated with the blood being pumped by the hose reel pump in comparable service by processing stored comparative experimental data associated with the centrifugal blood pump and the hose reel pump in comparable service, the experimental data including blood pressure, blood flow rate, and any resulting blood damage.

2. The method according to claim 1, wherein the centrifugal blood pump is arranged in an extracorporeal blood circulation of a blood treatment machine.

3. The method according to claim 2, wherein the blood treatment machine is a dialysis machine, a machine for supporting heart and lung activity, or a machine for supporting liver function.

4. The method according to claim 1, wherein the blood pressure upstream from the centrifugal blood pump is determined from the blood pressure downstream from the centrifugal blood pump and the rotational speed of the centrifugal blood pump, or wherein the blood pressure downstream from the centrifugal blood pump is determined from the blood pressure upstream from the centrifugal blood pump and the rotational speed of the centrifugal blood pump.

5. The method according to claim 1, wherein a preferred range for an operating point of the centrifugal blood pump is defined by a maximum blood pressure which depends on the pump rate upstream and/or downstream from the centrifugal blood pump, and wherein the centrifugal blood pump is triggered at a new pump rate such that the operating point of the centrifugal blood pump is within the allowed range, or a smallest possible interval between the operating point and the allowed range is established.

6. A device comprising
a control unit;
a centrifugal blood pump, which is controllable by the control unit; and
at least one sensor for detecting a blood pressure upstream and/or downstream from the centrifugal blood pump,
the control unit being configured such that an initial pump rate of the centrifugal blood pump is to be established or to be determined, and if the blood pressure upstream and/or downstream from the centrifugal blood pump and/or a difference in the blood pressures upstream and downstream from the centrifugal blood pump violate(s) a limit value which depends on the pump rate of the centrifugal blood pump, the pump rate of the centrifugal blood pump is adjusted until the limit value is no longer violated, or the difference in the blood pressure downstream from the centrifugal blood pump and the limit value, or upstream from the centrifugal blood pump and the limit value, decreases,
such that any damage to the blood being pumped by the centrifugal blood pump is less than or equal to the damage which would be associated with the blood being pumped by a hose reel pump in comparable service, and with an identical blood pressure downstream therefrom, with the control unit being configured to make a determination of any damage to the blood being pumped by the centrifugal blood pump relative to damage to the blood which would be associated with the blood being pumped by the hose reel pump in comparable service by processing stored comparative experimental data associated with the centrifugal blood pump and the hose reel pump in comparable service, the experimental data including blood pressure, blood flow rate, and any resulting blood damage.

7. The device according to claim 6, wherein the control unit is equipped to determine the blood pressure upstream from the centrifugal blood pump from the blood pressure downstream from the centrifugal blood pump and from the rotational speed of the centrifugal blood pump, or wherein the control unit is equipped to determine the blood pressure downstream from the centrifugal blood pump from the blood pressure upstream from the centrifugal blood pump and from the rotational speed of the centrifugal blood pump.

8. The device according to claim 6, wherein a preferred range for an operating point of the centrifugal blood pump which is defined by a maximum blood pressure, which depends on the pump rate, upstream and/or downstream from the centrifugal blood pump is stored, and wherein a new pump rate is established so that the operating point of the centrifugal blood pump is within the allowed range or the smallest possible interval between the operating point and the allowed range is established.

9. A blood treatment machine comprising an apparatus according to claim 6.

10. The blood treatment machine according to claim 9, further comprising an extracorporeal blood circulation having a blood treatment component.

11. The blood treatment machine according to claim 10, wherein at least parts of the extracorporeal blood circulation are configured as disposable parts.

12. The blood treatment machine according to claim 9, wherein the blood treatment machine is a dialysis machine, a machine for supporting heart and lung activity, or a machine for supporting liver function.

13. The blood treatment machine according to claim 10, wherein the extracorporeal blood circulation includes an arterial blood branch and a venous blood branch, and wherein the blood treatment component is a dialyser.

14. The device according to claim 6, wherein the control unit adjusts a new pump rate in an iterative process by varying the pump rate in a positive or negative direction in an incremental value thereof, and assesses after each iteration whether the adjustment has reduced a deviation of an operating point of the centrifugal blood pump from an optimum operating point.

15. The device according to claim 14, wherein the incremental value is 1% of the pump rate.

* * * * *